United States Patent [19]

Miller, III

[11] 4,093,037

[45] June 6, 1978

[54] HEAD ACTUATED CONTROL APPARATUS FOR BATTERY-POWERED WHEELCHAIR

[76] Inventor: William Wanet Miller, III, 2533 Hillegass St. Apt. 101, Berkeley, Calif. 94704

[21] Appl. No.: 684,759

[22] Filed: May 10, 1976

[51] Int. Cl.² ............................................. B60K 26/00
[52] U.S. Cl. ............................ 180/77 R; 180/DIG. 3; 297/DIG. 4; 297/330
[58] Field of Search ................. 180/6.5, DIG. 3, 77 R; 280/242 WC; 297/330, DIG. 4

[56] References Cited

U.S. PATENT DOCUMENTS

| | | | |
|---|---|---|---|
| 2,578,828 | 12/1951 | Nelson | 280/242 WC |
| 3,111,181 | 11/1963 | Yatich | 180/6.5 |
| 3,112,001 | 11/1963 | Wise | 180/6.5 |
| 3,374,845 | 3/1968 | Selwyn | 180/6.5 |
| 3,802,524 | 4/1974 | Seidel | 180/6.5 |
| 3,807,520 | 4/1974 | Chisholm | 180/6.5 |
| 3,882,949 | 5/1975 | Anderson | 280/242 WC |

FOREIGN PATENT DOCUMENTS 1,245,922  9/1971  United Kingdom .......... 180/DIG. 3

*Primary Examiner*—Joseph F. Peters, Jr.
*Assistant Examiner*—Donn McGiehan
*Attorney, Agent, or Firm*—Warren, Chickering & Grunewald

[57] ABSTRACT

Head actuated control apparatus for use in controlling the motion of a battery-powered wheelchair is disclosed. The apparatus is designed for use by the quadriplegic patient and includes a rheostat-type controller mounted to the wheelchair headrest and provided with cup means formed for engagement by the back of the head of the user or patient to enable displacement selectively in any one of four directions to control forward, rearward and turning motions. Additionally, the control apparatus includes head actuated switches mounted to the headrest proximate the cup and electrically connected to recline or raise the back of the wheelchair.

4 Claims, 5 Drawing Figures

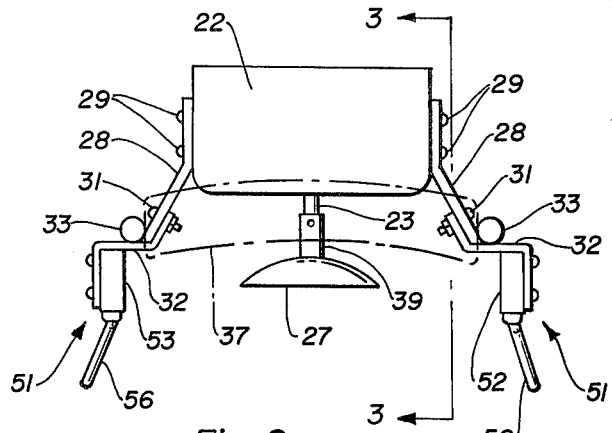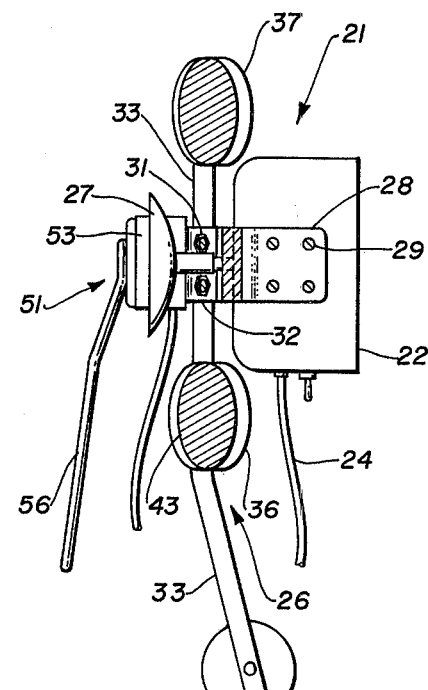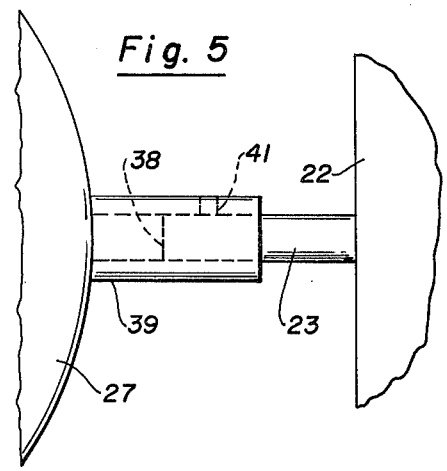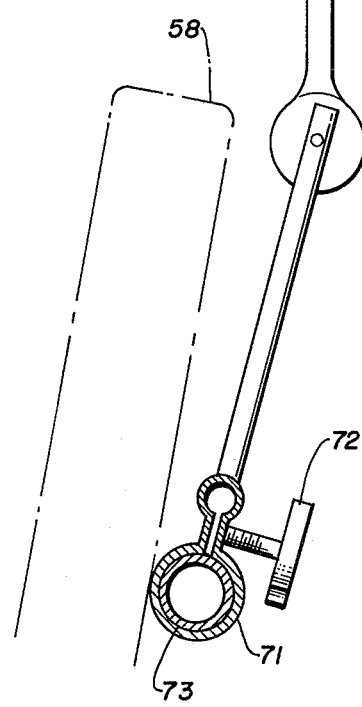

HEAD ACTUATED CONTROL APPARATUS FOR BATTERY-POWERED WHEELCHAIR

BACKGROUND OF THE INVENTION

Battery-powered wheelchairs have afforded the temporarily and permanently disabled person a new freedom of movement. For the paraplegic who has use of a hand or hands, control of movement of the wheelchair can be readily accomplished by means of hand-operated controls. A typical battery-powered or motorized wheelchair and a hand-operated controller is shown in U.S. Pat. No. 3,807,520. A similar wheelchair and hand-operated controller is shown in U.S. Pat. No. 3,802,524, with the controller in this patent additionally being formed for mounting on the back of the wheelchair for hand operation by an attendant walking behind the chair.

A quadriplegic cannot avail himself of the hand-operated controller, and attempts have been made to devise head-operated or actuated wheelchair controllers. One apparatus which has been commercially developed employs a chain rest which is positioned in front of the user and is connected to a rheostat-type controller. The chin rest is mounted to a lever arm which is universally mounted for displacement, and the chin of the user of the wheelchair is used to displace the control lever by pushing on the chin rest in a predetermined direction. Another similar commercially available controller employs a mouth stick or lever which is gripped between the teeth of the user. Again, the mouth stick is selectively displaced to control wheelchair motion through a rheostat controller.

While satisfactory for some applications, such commercially available wheelchair controllers for quadriplegics have been found to have substantial disadvantages. The basic problem that exists with chin rest and mouth stick controllers is that uneven and bumpy terrain can cause the user's head to bob or bounce, which is translated into spurious control signals to the wheelchair. Thus, uneven terrain can cause erratic movement which in turn feeds upon itself causing further spurious head movements and unwanted wheelchair control commands. Since the inertia of the person using the chair is forward and toward the control lever, it can be most difficult and sometimes impossible and highly dangerous to pull back away from the controller. This problem is accentuated on inclined surfaces. Thus, stopping when going downhill is uncertain and erratic, and gravity works against the user's head when going uphill.

Another head actuated wheelchair control system is shown in U.S. Pat. No. 3,374,845. In this system, a gravity based sensor is carried in a helmet worn by the disabled person. The helmet can then be tilted in predetermined direction so as to control wheelchair motion. In addition to being a relatively complex system, this approach similarly has the problem, which the patented system attempts to overcome by more apparatus, of bobbing, bouncing and weaving of the head of the patient when the chair is in motion. This head movement will again induce erratic wheelchair movement, which tends to feed back and accentuate or cause further head movement.

In addition to being able to control the forward or rearward motion of a wheelchair, it is highly desirable for the patient to be able to control his attitude or positioning in the chair by movements of portions of the chair. More particularly, it is highly desirable that the wheelchair user be able to periodically change the orientation of the back of the wheelchair with respect to the seat. Such change in orientation serves at least four purposes. First, it can allow the user to achieve the most comfortable position for him or her. Secondly, orientation of the back of the chair to different attitudes can greatly facilitate control of the wheelchair during motion, e.g., when going uphill or downhill. Thirdly, if the orientation of the back can be adjusted periodically about the most comfortable position, the incidence of decubitus ulcers resulting from pressure on body contact points can be reduced. Lastly, the chair back can be reclined to a fully prone position to enable resting. While wheelchairs which have backs that can be fully reclined to the prone position are well known, for example, see U.S. Pat. No. 3,111,181, the control mechanisms for such chairs have not been suitable for use by the quadriplegic.

Accordingly, it is an object of the present invention to provide a wheelchair control apparatus which can be used as a head actuatable control center for the motion and orientation of a wheelchair.

Another object of the present invention is to provide a head actuated control apparatus for use in controlling a battery-powered wheelchair which apparatus substantially eliminates the dynamic feedback from chair motion which can cause erratic movement.

It is a further object of the present invention to provide head actuated control apparatus for a wheelchair which will allow adjustment of the orientation of the wheelchair back to enable better control of the motion of the wheelchair.

It is a further object of the present invention to provide head actuated control apparatus for a battery-powered wheelchair which can be readily adjusted to accommodate the physical stature of disabled individuals.

It is a further object of the present invention to provide head actuated control apparatus for a battery-powered wheelchair which is relatively simple to construct and install, requires little training to master its use, is durable, and can be adapted for use on a wide variety of wheelchairs.

The head actuated control apparatus of the present invention has other objects and features of advantage, some of which will become more apparent from or are set forth in the following description and accompanying drawing.

SUMMARY OF THE INVENTION

The head actuated control apparatus is designed for use with a battery-powdered wheelchair and includes a rheostat controller formed to be electrically connected to control a wheelchair drive motor and formed with a selectively displaceable universal element to control forward, rearward and turning motion of the wheelchair. The improvement of the present invention is comprised, briefly, of cup means mounted to the universal element and formed to engage the back of the head of the user of the wheelchair, headrest means formed for selective support of the head of the user, and the rheostat controller being mounted proximate the headrest with the cup means positioned for selective engagement and displacement of the cup means by the back of the head of the user. Additionally, switch means is mounted to the headrest proximate the cup and is electrically connected to a wheelchair back reclining mechanism, the switch means being further formed and mounted to be selectively engaged by the head of the user to recline and raise the back of the wheelchair.

DESCRIPTION OF THE DRAWING

FIG. 2 is a top plan view of the control apparatus of FIG. 1.

FIG. 3 is a side elevational view in cross-section taken substantially along the plane of line 3—3 in FIG. 2.

FIG. 5 is a fragmentary, enlarged view of the cup means-rheostat connection constructed in accordance with the present invention.

DESCRIPTION OF THE PREFERRED EMBODIMENT

Figures 1, 4:
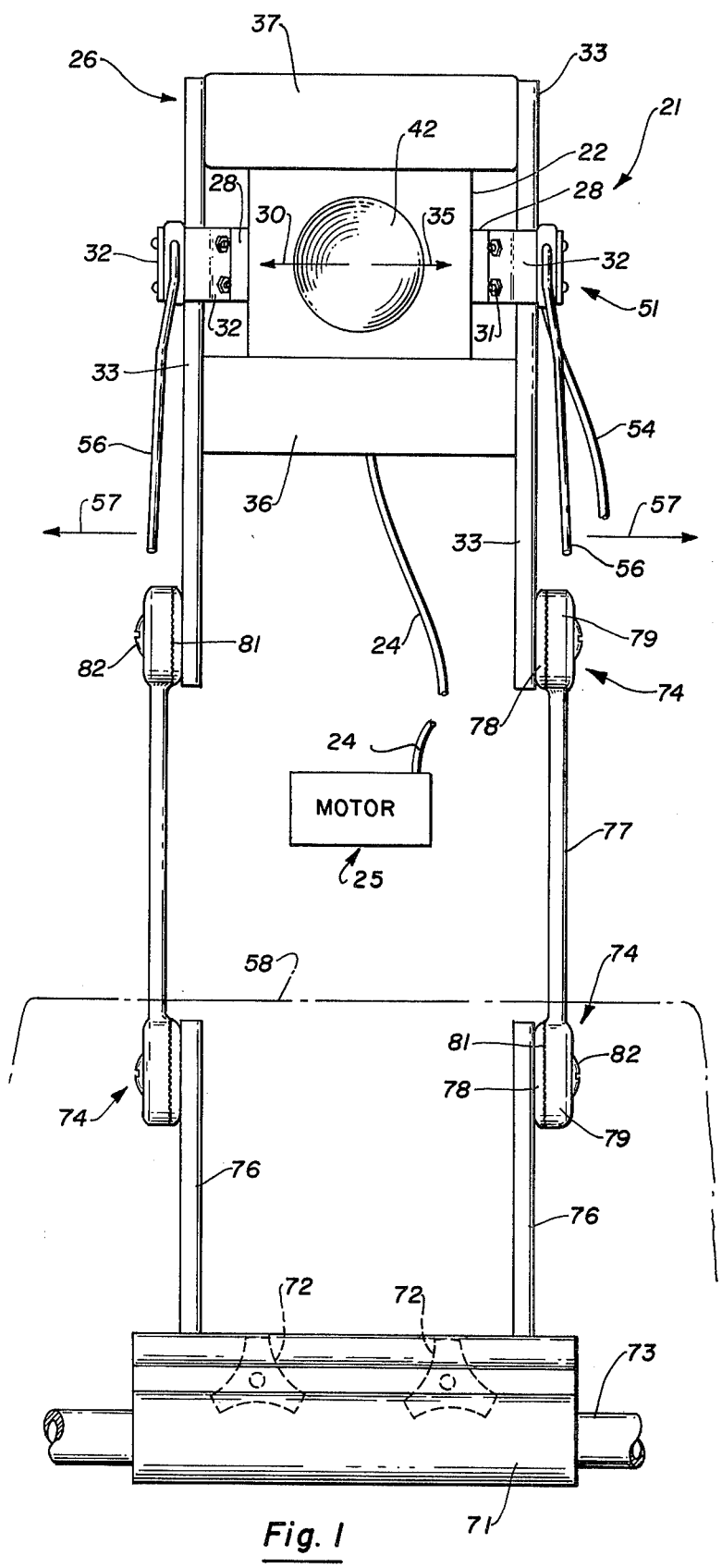
FIG. 1 is a front elevational view of a wheelchair headrest and control apparatus constructed in accordance with the present invention.
FIG. 4 is a fragmentary exploded perspective view of a portion of the headrest structure of FIG. 1.

Referring now to the drawing, the control apparatus, generally designated 21, of the present invention can be set forth in detail. The apparatus is used for controlling the motion of a battery-powered wheelchair (not shown) of conventional and well known construction. The apparatus includes a rheostat controller 22 formed to be electrically connected through conductor means 24 to control a wheelchair drive motor or motor means 25, schematically shown. There are several rheostat-type wheelchair controllers on the market which are suitable for use in the wheelchair of the present invention. One such controller 22 is manufactured by Everest & Jennings, Inc. of Los Angeles, Calif. Rheostat controllers commonly include an element or shaft 23 which is mounted by a universal joint to controller 22 for displacement in any radial direction with respect to the longitudinal axis of shaft 23. The rheostat portion of the controller converts the direction and amount of displacement of shaft or universal element 23 into command signals which are transmitted through conductor means 24 to the wheelchair drive motors.

Typically, downward displacement of shaft 23 (as shown in FIG. 1) will cause forward motion of the chair, while upward displacement will cause rearward motion. Since most wheelchairs include two independent drive motors, the controller can be used to drive either of the two drive wheels of the wheelchair independently. Most controllers are electrically connected to the drive motors so that displacement to the left of shaft 23 can be translated by the rheostat controller into a signal which will cause turning to the left by the wheelchair drive motors. Contrarily, in prior controllers displacement of shaft 23 to the right will cause turning of the wheelchair to the right.

As thus far described, the rheostat controller forming part of the control apparatus of the present invention is well known in the prior art and is not regarded as a novel portion of the present invention. In prior art devices, however, the universal element 23 has either been hand-operated or positioned for head operation in the direction of the inertia of the user when the wheelchair is in motion, that is, in front of the head of the user. As is the case with most vehicles, wheelchairs are only occasionally required to move in a rearward direction, and then the motion is usually accomplished relatively slowly and cautiously. Since forward motion of the chair comprises the vast bulk of the time during which the chair is in motion, the inertia of the disabled person in a wheelchair is almost always in a forward direction. Moreover, bumps and irregularities in the surface over which the chair is traveling usually disrupt the forward motion of the chair with the result that the inertia of the disabled person tends to carry him forward, a phenomenon which also occurs during braking and which is exaggerated on downward incliners. The inertia at rest is not too significant since most wheelchairs cannot accelerate rapidly.

In the present invention the control apparatus is positioned so that the normal forward inertia during motion of the wheelchair causes the disabled person to be in a fail-safe situation. Control apparatus 21 includes headrest means, generally designated 26, which is not per se new, but in the improved control apparatus of the present invention, rheostat controller 22 is mounted proximate headrest means 26 with cup means 27, mounted to universal element 23, positioned for selective engagement and displacement by the back of the head of theuser. Instead of positioning universal element or shaft 23 in front of the user where the inertia of the user causes undesirable dynamic feedback and spurious control signals, in the control apparatus of the present invention, the universal element is positioned behind the head of the user; and cup means 27, formed to engage the back of the head of the user, is mounted to the universal element. When the wheelchair hits a bump or discontinuity in the surface over which the chair rides, the tendency is for the inertia of the user to cause his head to move away from cup means 27, which will automatically cause universal element 23 to move to the neutral position (shown in the figures), which in turn automatically slows the wheelchair.

Minor bumps and discontinuities can, of course, be absorbed by the wheelchair user, while most major discontinuities or bumps which are encountered will tend to cause the head of the wheelchair user to be moved away from the controller, not into it. Most of the bumps which would not cause the user's head to go forward, would move the same either upwardly or downwardly, and only in the most severe and abnormal cases would the user's head be moved rearwardly into the controller. In those instances, the tendency is to displace cup 27 upwardly, causing showing of the chair as the motor goes into reverse, and the inertia of the slowing process causes the user's head to move away from cup 27. Thus, even in the worst instance, the user's head will only tend to slow the chair motion, which pulls his head away from the controller.

In addition to mounting the controller proximate headrest assembly 26 for engagement by the back of the user's head, the controller of the present invention is preferably electrically connected to the drive motors in a manner such that displacement of cup 27 in the direction of arrow 30 causes turning of the chair in the opposite direction. Similarly, displacement of cup 27 in the direction of arrow 35 also causes turning of the wheelchair in the opposite direction. This reversing of the command signals of the wheelchair controller is provided to enable the disabled person to be able to face in the direction which he is turning when using the present controller. Thus, as the user turns his head to the right, the back of his head pivots to the left and displaces cup 27 in the direction to arrow 35, and the wheel-chair turns to the right, the direction which he is facing.

Mounting of controller 22 proximate the headrest for displacement of cup 27 by the back of the head of the user can be accomplished in a number of ways. It is preferable, however, to provide a pair of brackets 28 which are fastened at one end by fasteners 29 to controller 22 and are fastened at an opposite end by fasteners 31 to a bracket 32 which is secured to vertical headrest posts 33. Bracket 32 can be secured to posts 33 by a number of different techniques, including fasteners, welds, etc. Additionally, brackets 32 can be adjustably secured to posts 33, as for example by providing a frictional clamp around post 33 (not shown). In most instances, however, it is not necessary to adjust the vertical positioning of controller 23 and cup means 27 since the remainder of the headrest is constructed to enable vertical adjustment of the entire headrest assembly, as will be set forth more fully hereinafter. Also mounted to posts 33 are first and second padded headrest elements 36 and 37, which extend transversely of the posts at positions below and above cup means 27, respectively.

In order to accommodate each individual's preference and to enhance manipulation of cup 27, it is preferable that cup 27 be adjustably mounted on the distal end 38 of control lever or shaft 23 so as to enable selective adjustment of the position of cup 27 with respect to the transverse elements 36 and 37 of headrest 26. This can be accomplished by providing cup means 27 with a telescoping tubular element 39 which is mounted over distal end 38 of shaft 23 and secured in place by a locking screw 41 or the like. Using this adjustment, cup 27 can be moved inwardly or outwardly from controller 23 so as to position the same inwardly or outwardly of headrest elements 36 and 37 at the most convenient position for the user. It has been found that a position at which the concaved surface 42 is about even with or slightly inwardly of the surface 43 of transverse headrest pad 36 is preferable for maximum control and comfort.

In normal use, headrest pads 36 and 37 are not constantly being used for support of the disabled person's head. Instead, they provide cushions against upward or downward motion of the head when going over a bump, and the lower headrest element 36 can be used to support the head when the chair is reclined, as will be set forth more fully hereinafter. The normal orientation of the chair back results in the headrest being near vertical, and the head of the user requires little support. The cup means 27 also allows the user to rest his head against the cup in the neutral position, to the extent this may be desired.

In order to provide still further improved control over the forward motion of the wheelchair, the control apparatus of the present invention further preferably includes switch means, generally designated 51, mounted to headrest means 26 proximate control cup 27. Switch means 51 preferably includes a first switch 52 mounted to headrest 26 on a first side of cup 27 and a second switch 53 mounted to headrest 26 on a second side of the control cup. Switches 52 and 53 are formed for electrical connection through conductor means 54 to a wheelchair back reclining mechanism (not shown). A number of different types of wheelchair reclining mechanisms are suitable for use with the present invention. Typical of these devices is one produced by Duff-Norton Company, Charlotte, N.C., and sold under the trademark MINI PAC ACTUATOR.

Switch means 51 can also take numerous forms, but it is preferably a contact switch biased to an open position and formed so that an actuating lever or element 56 can be displaced, preferably outwardly in the direction of arrows 57 so as to switch on the reclining mechanism and either raise or lower the back 58 (partially shown in phantom in FIGS. 1 and 3) of the wheelchair. The positioning of switch means 51 in close proximity to control cup means 27 affords the wheelchair user with a complete control center which can be head actuated to recline the chair as well as control forward motion of the chair.

It has been found that the ability to control the orientation of the back of the chair with respect to the seat is of very substantial importance in controlling the motion of the wheelchair. In the control apparatus of the present invention, switch means 51 affords a mechanism to orient the back of the chair in a manner which gives the user the greatest control over displacement of the control cup 27. Thus, when traveling uphill, for example, the back of the chair can be raised beyond the normal position so as to incline the upper body of the wheelchair user to a more vertical position so that the disabled person does not have to fight gravity and does not have his head thrust by gravity against the control cup. Similarly, when going downhill, switch means 51 can be used to recline the chair so that the back of the disabled person is in a more nearly vertical position, rather than a tilted forward position. The ability to recline or raise the back of the chair to accommodate the environment by simple head-actuated switches greatly enhances overall chair control.

In addition, switch means 51 can be used to place the back of the chair at the most comfortable position for each individual user when the chair is on a level surface. Moreover, a simple sideward motion of the head which displaces switches 54 or 56 away from cup 27 in the directions indicated by arrows 57 can be used to slightly adjust the chair to eliminate pressure points which would otherwise exist from prolonged sitting of the disabled person in the chair. Such slight shifting about the optimum back position reduces the incidence of decubitus ulceration.

Finally, it has been found highly advantageous to be able to recline the wheelchair back to a fully prone position, that is, level with the seat of the chair. This reclining of the back can optionally be combined with a mechanism for raising the leg supporting portion of the chair to a level position with the seat. As the back of the wheelchair is reclined, however, the relative position between the back of the head of the user and cup 27 will become vertically displaced. Since the user's body does not shift upon the seat of the wheelchair, reclining of the back of the chair causes some shifting along the back and causes the head to drop down upon lower transverse headrest element 36. In this position, the transverse element provides full support for the disabled person's head without the need to contact control cup 27 for support. When the head of the user is shifted downwardly during reclining with respect to the headrest, the actuating levers or elements 56 must extend in a direction parallel to the back of the chair toward the seat of the chair over a distance sufficient to enable the head of the user to engage and displace the actuating elements even in the fully reclined position. As can be seen in FIGS. 1 and 3, therefore, actuating elements 56 extend downwardly to a position below transverse head supporting pad 36.

Finally, it is also an important feature of the present invention that the control apparatus be readily adjustable to accommodate the individual stature and personal preferences of each user. This is particularly advantageous when the controller of the present invention is used in a hospital wheelchair, or a chair that has to be used by several individuals. Most control apparatus for quadriplegics has heretofore required substantial customization and individual "fitting" of the wheelchair controller to the individual. As a result, one chair cannot normally or conveniently be used by a multiplicity of disabled users. In the apparatus of the present invention, however, the headrest assembly can be rapidly adjusted to the individual user. The headrest assembly includes a mounting clamp structure 71 having manually engageable clamping screws 72 provided thereon so as to enable frictional engagement of a transverse bar or tabular member 73 forming a part of the back support structure for the chair. Some chairs include such a horizontally extending bar, and the mountng clamp 71 is suitable for mounting to the same at virtually any lateral position along the back of the chair, in accordance with the user's preference. As will be understood, other means for mounting the headrest assembly to the back of the chair can be provided.

The headrest assembly further preferably includes angular adjustment means 74 which connects vertically extending post or tube members 76 and 77, as well as connecting vertical post 33 to intermediate post or link 77. FIG. 4 shows the details of construction of such adjustable connection means, which can be seen to be comprised of a pair of mating circular portions 78 and 79, each having interfitting teeth 81. The two positions are held together in an interlocked orientation by fastener 82 or the like. By varying the angle at which clamp 71 is clamped to the chair back element 73 and further the angles at which the vertical posts 33, 76 and 77 are secured with respect to each other, a wide variety of differing vertical and angular orientations of the control cup 27 and headrest assembly 26 can be achieved. Thus, the headrest mounting means can be used to selectively vary the height, angular orientation and lateral position of the headrest with respect to the back of the wheelchair so as to accommodate the individual and place the control apparatus at the optimum position for control of the wheelchair.

What is claimed is:

1. Control apparatus for use in controlling the position of a reclinable back on a battery-powered wheelchair having a headrest and an electrically powered back reclining mechanism, said apparatus including a first switch and a second switch formed for mounting proximate said headrest, said first switch being formed for electrical connection to said back reclining mechanism to effect reclining of said back and said second switch being formed for electrical connection to said back reclining mechanism to effect raising of said back, said first switch and said second switch each including actuating elements formed for engagement by the head of the user of said wheelchair, wherein the improvement in said control apparatus comprises:

said actuating elements being formed for mounting proximate said headrest to extend in a direction generally parallel to the back of the wheelchair over a distance enabling engagement thereof by the head of the user when the back of the wheelchair is in the fully reclined position.

2. Wheelchair control apparatus as defined in claim 1 wherein, said apparatus includes a controller formed for electrical connection to a drive motor for said wheelchair and formed for mounting proximate said headrest and for actuation by engagement thereof with the head of the user of said wheelchair; and said headrest includes an element positioned to support the head of the user out of engagement with said controller when in the fully reclined position.

3. Control apparatus for use in controlling the motion of a wheelchair having a drive motor and battery means electrically connected thereto, said control apparatus including, a controller adapted for electrical connection to said drive motor and provided with a displaceable universal element mounted to said controller for control of the motion of said wheelchair by displacement of said universal element in selected directions, and headrest means formed for support of the head of the user of said wheelchair, said controller being mounted proximate and headrest means, and said universal element being adapted for engagement by the back of the head of the user of said wheelchair, wherein the improvement in said apparatus comprises:

said headrest means includes a first padded element positioned below said universal element for support of the head of the user and a second padded element positioned above said universal element.

4. Control apparatus for use in controlling the motion of a wheelchair, said wheelchair including battery means, a seat back, a back reclining mechanism electrically connected to said battery means and coupled to said seat back and formed to raise and lower said seat back, and a wheelchair drive motor electrically connected to said battery; and said control apparatus including a controller adapted for electrical connection to said drive motor and provided with a displaceable universal element mounted to said controller to universal element the motion of said wheelchair upon displacement of said universalelement in selected directions, and headrest means formed for support of the head of the user of said wheelchair, said controller being mounted proximate said headrest means and said universal element being adapted for engagement by the back of the head of the user of said wheelchair to enable control of the motion of said wheelchair, wherein the improvement in said apparatus comprises:

switch means mounted to said headrest means proximate said universal element, said switch means being adapted for electrical connection to said wheelchair back reclining mechanism, said switch means further being adapted and mounted for selective engagement by the head of the wheelchair user for actuation of said switch means to recline and raise said back of said wheelchair.

* * * * *

UNITED STATES PATENT AND TRADEMARK OFFICE
CERTIFICATE OF CORRECTION

PATENT NO. : 4,093,037
DATED : June 6, 1978
INVENTOR(S) : WILLIAM WANET MILLER III It is certified that error appears in the above-identified patent and that said Letters Patent are hereby corrected as shown below:

In column 1, line 23, delete "chain" and insert ---chin---.

In column 7, line 13, delete "tabular" and insert ---tubular---.

In claim 4, column 8, lines 41 and 42, delete "universal element" and insert ---control---.

In claim 4, column 8, line 43, change "universalelement" to ---universal element---.

Signed and Sealed this

Twelfth Day of December 1978

[SEAL]

Attest:

RUTH C. MASON
Attesting Officer

DONALD W. BANNER
Commissioner of Patents and Trademarks